United States Patent

Hiemisch et al.

[11] Patent Number: 5,571,211
[45] Date of Patent: Nov. 5, 1996

[54] TUBULAR ADAPTER FOR A PROSTHETIC LIMB

[75] Inventors: Christian Hiemisch, Duderstadt; Markus Holzapfel, Osterode, both of Germany

[73] Assignee: Otto Bock Orthopadische Industrie Besitz-und Verwaltungs-Kommanditgesellschaft, Germany

[21] Appl. No.: 439,380

[22] Filed: May 11, 1995

[30] Foreign Application Priority Data

May 30, 1994 [DE] Germany ............................ 9408804 U

[51] Int. Cl.⁶ ..................................................... A61F 2/62
[52] U.S. Cl. ................................................ 623/38; 403/373
[58] Field of Search .................................. 623/38; 403/11, 403/12, 373; 285/49, 373

[56] References Cited

U.S. PATENT DOCUMENTS

| | | | |
|---|---|---|---|
| 1,579,648 | 4/1926 | Crickmer | 285/373 X |
| 3,659,294 | 5/1972 | Glabiszewski | |
| 4,529,332 | 7/1985 | Glabiszewski | 623/38 X |
| 4,819,974 | 4/1989 | Zeidler | 285/373 |
| 5,443,527 | 8/1995 | Wilson | 623/49 |

Primary Examiner—David H. Willse
Attorney, Agent, or Firm—Whitham, Curtis, Whitham & McGinn

[57] ABSTRACT

The invention relates to a tubular adapter for clamping connection with the end of a tubular part (4) of a modular prosthesis. The adapter includes an axially slotted connecting sleeve (2) circumferentially clampable by means of a clamping bolt or the like and intended to receive tube end (4), with one end of said sleeve abutted by an annular coupling section (3) preferably having on its circumference four equally spaced threaded holes (5), each hole being designed to receive a coupling and adjusting bolt (clamping bolt) and having an annular ball socket (6) provided endwise to engage a ball collar of an adjusting core. The socket extends in the coupling position on a projection designed as a multi-surface pyramid into the clamping area of the clamping bolts.

To improve the connection between the tubular adapter and the tubular part, it is proposed according to the invention that free end section (7) of connecting sleeve (2) opposite coupling section (3) be provided on its inner annular surface with a plastic clamping cuff (8).

5 Claims, 2 Drawing Sheets

5,571,211

TUBULAR ADAPTER FOR A PROSTHETIC LIMB

BACKGROUND OF THE INVENTION

1. Field of the Invention

The invention relates to a tubular adapter for clamping connection with the end of a tubular part of a modular prosthesis, comprising an axially slotted connecting sleeve, said sleeve being circumferentially clampable by means of a clamping bolt or the like and designed to receive the end of a tube, at one end of which sleeve an annular coupling section abuts, said section preferably having on its circumference four equally spaced threaded holes, each to receive a coupling and adjusting bolt (clamping bolt) and having an endwise annular ball socket to engage a ball collar of an adjusting core, said socket, in the coupling position, extending on a projection shaped as a multi-surface pyramid into the clamping area of the clamping bolt.

2. Description of the Prior Art

U.S. Pat. No. 3,659,294 shows in FIGS. 3 and 4, a projection of an adjusting core that is designed as a four-surface pyramid, mounted standing on its point and centered with respect to the ball collar. In the coupling position, this projection extends through the annular ball socket of the adapter into the vicinity of the clamping bolts, each of which contacts one of the pyramid surfaces approximately perpendicularly, and said bolts are therefore arranged with their axes at an acute angle to the cross-sectional plane of the tube.

SUMMARY OF THE INVENTION

The goal of the invention is to improve the connection between the tubular adapter and the tubular part.

This goal is achieved according to the invention by virtue of the fact that the free end section of the connecting sleeve opposite the coupling section is provided with a plastic clamping cuff on its inner annular surface.

This invention is based on the following facts: By virtue of the clamping process, the tubular part is impacted at precisely the point at which the stresses applied by the loading of the prosthesis are greatest. In addition, it has been found that in known embodiments, each alternation in load results in a relative movement between the connecting sleeve and the tubular part, damaging the aluminum tube.

On the other hand, according to the invention, clamping is no longer performed directly on the tube end but at a distance therefrom, so that the tube section located between the plastic clamping cuff and the coupling section can be subjected to elastic deformation. In the area of maximum relative movement between the connecting sleeve and the tube end, metallic contact between these two parts is suppressed by the plastic clamping cuff. Dynamic bending tests have shown that the lifetime of these components is considerably prolonged as a result.

BRIEF DESCRIPTION OF THE DRAWINGS

The drawings show an embodiment of the invention that serves as an example.

DETAILED DESCRIPTION OF THE PREFERRED EMBODIMENTS OF THE INVENTION

Figure 1:
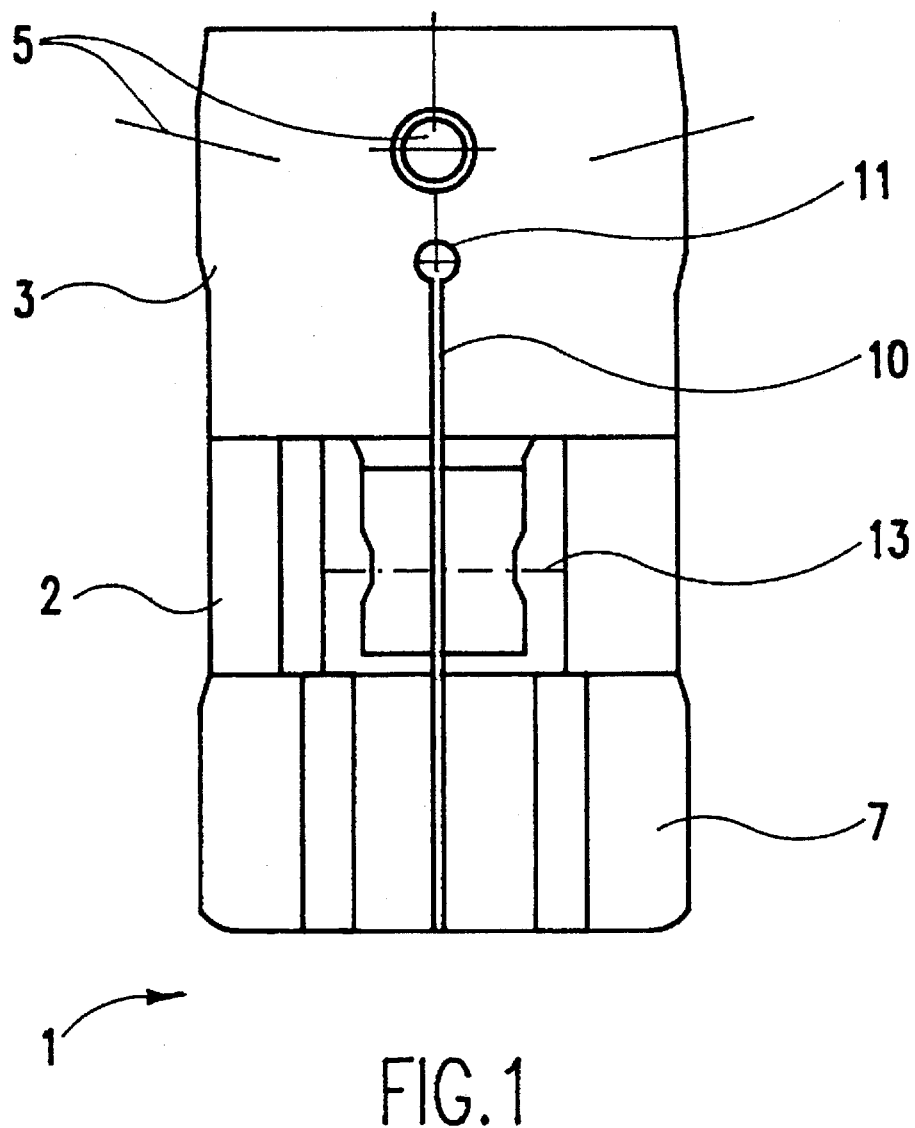
FIG. 1 shows a tubular adapter in a side view.
Figure 2:
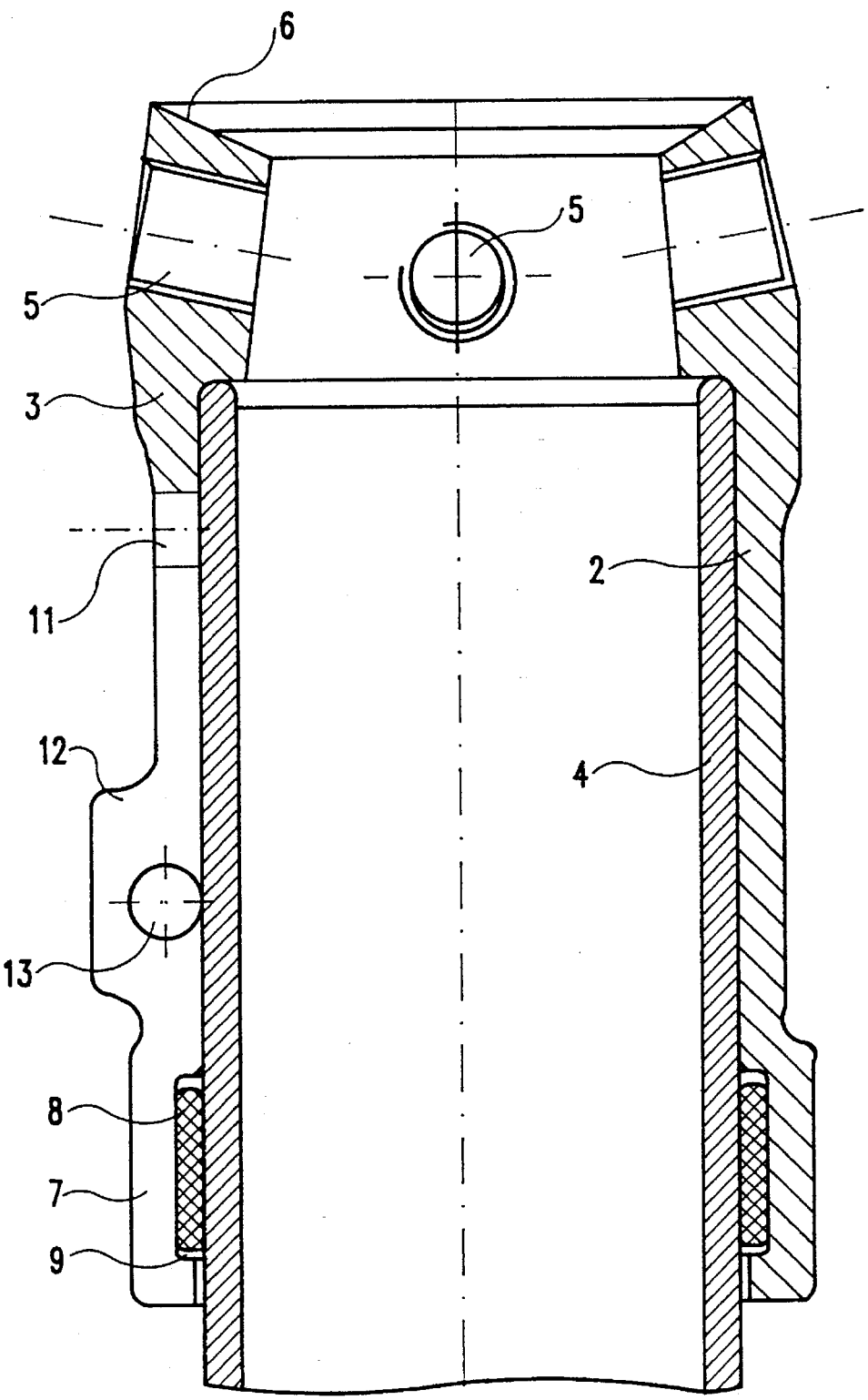
FIG. 2 shows, on an enlarged scale, a lengthwise section through the tubular adapter according to FIG. 1 with a tubular part inserted.

The figures show a tubular adapter 1 composed of a connecting sleeve 2 and an annular coupling section 3 abutting one end of said sleeve. FIG. 2 shows that connecting sleeve 2 serves to receive an inserted tube end 4.

Coupling section 3 has on its circumference four equally spaced threaded holes 5, each to receive a coupling and adjusting bolt (clamping bolt) not shown in greater detail in the drawing, and, endwise, an annular ball socket 6 to receive a ball collar of an adjusting core, not shown in greater detail in the drawing, said core extending in the coupling position on a projection designed as a multi-surface pyramid into the clamping area of the clamping bolts.

The clamping bolts perform the coupling between the adapter part and the adjusting core. At the same time, however, the clamping bolts serve for adjusting the central axis of the adjusting core with respect to the tube axis of the tubular part. By loosening one clamping bolt and tightening the opposite clamping bolt, the adjusting core can be tilted with respect to the tubular adapter in a given plane. By appropriate adjustment of the other two clamping bolts, located opposite one another, pivoting can be performed in a second plane perpendicular to the first plane, with the ball collar of the adjusting core in each case sliding in the annular ball socket of the adapter part.

The tubular adapter is usually made of steel or titanium, while the tubular part is made of aluminum. In the known embodiment, each end of the tubular part is slid into a tubular adapter, with the connection being made in the form of a press fit or a clamping connection. In the latter case, the tubular adapter is provided with a clamping strap that can be tightened by means of a bolt.

Connecting sleeve 2 is provided with an end section 7 at its end opposite coupling section 3, said section 7 surrounding a plastic clamping cuff 8 embedded in an annular groove 9 of end section 7. Plastic clamping cuff 8 can be placed loosely in annular groove 9. The dimensions of plastic clamping cuff 8 and/or annular groove 9 are chosen so that clamping takes place over the entire axial length of connecting sleeve 2, but especially over the axial length of plastic clamping cuff 8. "The axial length of the plastic clamping cuff roughly corresponds to one-fifth the axial length of the connecting sleeve".

Connecting sleeve 2 has an axial slot 10 that merges with an unloading bore 11. On both sides of axial slot 10, connecting sleeve 2 is provided with a tab 12, said tabs each having a bore 13, said bores being flush with one another, to receive a clamping bolt, not shown in greater detail.

While the invention has been described in terms of its preferred embodiments, those skilled in the art will recognize that the invention can be practiced with modification within the spirit and scope of the appended claims.

We claim:

1. Tubular adapter for clamping connection with an end of a tubular part of a modular prosthesis, comprising a connecting sleeve including an axial slot, said connecting sleeve being circumferentially clampable by a clamping member which is connected to said connecting sleeve across said axial slot, said connecting sleeve having an opening to receive said end of said tubular part, a first end of said connecting sleeve abutting upon an annular coupling section which includes on its circumference four equally spaced threaded holes, each threaded hole for receiving a coupling and adjusting bolt, said annular coupling section comprising an annular ball socket provided endwise to abut a ball collar of an adjusting core and a clamping area positioned adjacent said annular ball socket, said connecting sleeve including a second end located opposite said coupling section, said second end of said connecting sleeve including an inner annular surface, and wherein a plastic clamping cuff is positioned on said inner annular surface of said second end of said connecting sleeve, wherein said plastic clamping cuff is a separate ring which is embedded in a region of said second end of said connecting sleeve.

2. Tubular adapter for clamping connection with an end of a tubular part of a modular prosthesis, comprising a connecting sleeve including an axial slot, said connecting sleeve being circumferentially clampable by a clamping member which is connected to said connecting sleeve across said axial slot, said connecting sleeve having an opening to receive said end of said tubular part, a first end of said connecting sleeve abutting upon an annular coupling section which includes of its circumference four equally spaced threaded holes, each threaded hole for receiving a coupling and adjusting bolt, said annular coupling section comprising an annular ball socket provided endwise to abut a ball collar of an adjusting core and a clamping area positioned adjacent said annular ball socket, said connecting sleeve including a second end located opposite said coupling section, said second end of said connecting sleeve including an inner annular surface, and wherein a plastic clamping cuff is positioned on said inner annular surface of said second end of said connecting sleeve, wherein an axial length of said plastic clamping cuff roughly corresponds to one-fifth of an axial length of said connecting sleeve.

3. A tubular adapter for use in a modular prosthesis, comprising:
- a connecting sleeve having first and second ends, and a cylindrical bore extending within said connecting sleeve from said second end to said first end for receiving a tubular part of a modular prosthesis;
- an axial slot in said connecting sleeve extending from said second end of said connecting sleeve to a point near said first end of said connecting sleeve;
- a circumferential clamping means connected to an external surface of said connecting sleeve and positioned to clamp across said axial slot in said connecting sleeve;
- an annular coupling means positioned at said first end of said connecting sleeve, said annular coupling means including
  - an annular ball socket designed to abut a ball collar of an adjusting core and to receive a multi-surface pyramid shaped core which extends from said ball collar,
  - an interior clamping region positioned adjacent said annular ball socket, and
  - a plurality of equally circumferentially spaced threaded openings extending from an exterior surface of said annular coupling means to said interior clamping region; and
- a plastic clamping cuff positioned on an inner surface of said cylindrical bore of said connecting sleeve in a region of said second end of said connecting sleeve, said region of said second end of said connecting sleeve having an annular groove formed therein and wherein said plastic clamping cuff is matched in size to said annular groove, said plastic clamping cuff eliminating metallic contact between said tubular part of said modular prosthesis and said inner surface of said connecting sleeve in said region of said second end of said connecting sleeve.

4. A tubular adapter for use in a modular prosthesis comprising:
- a connecting sleeve having first and second ends, and a cylindrical bore extending within said connecting sleeve from said second end to said first end for receiving a tubular part of a modular prosthesis;
- an axial slot in said connecting sleeve extending from said second end of said connecting sleeve to a point near said first end of said connecting sleeve;
- a circumferential clamping means connected to an external surface of said connecting sleeve and positioned to clamp across said axial slot in said connecting sleeve;
- an annular coupling means positioned at said first end of said connecting sleeve said annular coupling means including
  - an annular ball socket designed to abut a ball collar of an adjusting core and to receive a multi-surface pyramid shaped core which extends from said ball collar,
  - an interior clamping region positioned adjacent said, annular ball socket, and
  - a plurality of equally circumferentially spaced threaded openings extending from an exterior surface of said annular, coupling means to said interior clamping region; and
- a plastic clamping cuff positioned on an inner surface of said cylindrical bore of said connecting sleeve in a region of said second end of said connecting sleeve, said region of said second end of said connecting sleeve having an annular groove formed therein and wherein said plastic clamping cuff is a coating positioned within said annular groove, said plastic clamping cuff eliminating metallic contact between said tubular part of said modular prosthesis and said inner surface of said connecting sleeve in said region of said second end of said connecting sleeve.

5. A tubular adapter for use in a modular prosthesis, comprising:
- a connecting sleeve having first and second ends, and a cylindrical bore extending within said connecting sleeve from said second end to said first end for receiving a tubular part of a modular prosthesis:
- an axial slot in said connecting sleeve extending from said second end of said connecting sleeve to a point near said first end of said connecting sleeve;
- a circumferential clamping means connected to an external surface of said connecting sleeve and positioned to clamp across said axial slot in said connecting sleeve;
- an annular coupling means positioned at said first end of said connecting sleeve said annular coupling means including
  - an annular ball socket designed to abut a ball collar of an adjusting core and to receive a multi-surface pyramid shaped core which extends from said ball collar.
  - an interior clamping regions positioned adjacent said annular ball socket, and
  - a plurality of equally circumferentially spaced threaded openings extending from an exterior surface of said annular coupling means to said interior clamping region; and
- a plastic clamping cuff positioned on an inner surface of said cylindrical bore of said connecting sleeve in a region of said second end of said connecting sleeve wherein said plastic clamping cuff has an axial dimension which is approximately one fifth of an axial length of said connecting sleeve, said plastic clamping cuff eliminating metallic contact between said tubular part of said modular prosthesis and said inner surface of said connecting sleeve in said region of said second end of said connecting sleeve.

* * * * *